US00PP35210P2

(12) United States Plant Patent
Kamstra

(10) Patent No.: US PP35,210 P2
(45) Date of Patent: Jun. 6, 2023

(54) ***LAVANDULA* PLANT NAMED 'LABZ0012'**

(50) Latin Name: *Lavandula stoechas*
Varietal Denomination: LABZ0012

(71) Applicant: SYNGENTA CROP PROTECTION AG, Basel (CH)

(72) Inventor: Silvan Adelmar Kamstra, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/944,237

(22) Filed: Sep. 14, 2022

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./263.1, 445
See application file for complete search history.

*Primary Examiner* — Karen M Redden
(74) *Attorney, Agent, or Firm* — Dale Skalla

(57) ABSTRACT

A new *Lavandula* plant named 'LABZ0012', particularly distinguished by numerous purple sterile large bracts, purple black flowers, medium green foliage without greyish hue, a compact sized plant with a rounded, mounding habit, early to flower and long flowering.

1 Drawing Sheet

Figure 1:
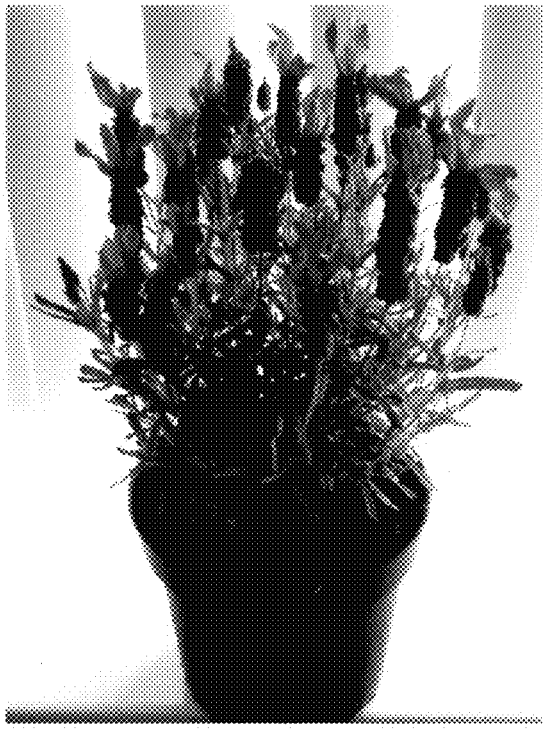

Latin name of the genus and species of the plant claimed: *Lavandula stoechas.*

Varietal denomination: 'LABZ0012'.

BACKGROUND OF THE NEW PLANT

The present invention comprises a new *Lavandula*, botanically known as *Lavandula stoechas*, and hereinafter referred to by the variety name 'LABZ0012'.

'LABZ0012' is a product of a planned breeding program. The new cultivar has numerous purple sterile large bracts, purple black flowers, medium green foliage without greyish hue, a compact sized plant with a rounded, mounding habit, early to flower and long flowering.

'LABZ0012' originated from a pollination made in 2016 in a greenhouse in Enkhuizen, The Netherlands. The plant originates from an inbreeding from a hybrid cross made in 2013 in Enkhuizen, The Netherlands. Therefore, the female and male parent is the same unpatented, proprietary plant designated 'PERAW2041-(4). 2V', with a purple flower and a strong habit.

The resultant seed was sown in January 2017 and grown outdoors in Enkhuizen, The Netherlands. 'LABZ0012' was selected as a single flowering plant within the progeny of the stated cross early July 2017 in Enkhuizen, The Netherlands.

The first act of asexual reproduction of 'LABZ0012' was accomplished when vegetative stem cuttings were propagated from the initial selection in September 2017 in a greenhouse in Enkhuizen, The Netherlands.

BRIEF SUMMARY OF INVENTION

Horticultural examination of plants grown from cuttings of the plant initiated September 2017, and continuing thereafter, has demonstrated that the combination of characteristics as herein disclosed for 'LABZ0012' are firmly fixed and are retained through successive generations of asexual reproduction.

'LABZ0012' has not been observed under all possible environmental conditions. The phenotype may vary significantly with variations in environment such as temperature, light intensity and day length.

A Plant Breeder's Right for this cultivar has not yet been applied for. 'LABZ0012' has not been made publicly available prior to the effective filing date of this application, notwithstanding any disclosure that may have been made less than one year prior to the effective filing date of this application by the inventor or another who obtained 'LABZ0012' directly from the inventor.

The following traits have been repeatedly observed and are determined to be basic characteristics of the new variety. The combination of these characteristics distinguishes this *Lavandula* as a new and distinct variety.

BRIEF DESCRIPTION OF THE PHOTOGRAPHS

The accompanying photographic drawings show typical flower and foliage characteristics of 'LABZ0012' with colors being as true as possible with an illustration of this type. The photographic drawings show in FIG. 1 a flowering plant of the new variety and in FIG. 2 a close up of the flower(s).

DETAILED BOTANICAL DESCRIPTION

The plant descriptions and measurements were taken outdoors in Enkhuizen, The Netherlands on Aug. 4, 2022 on about 14 weeks old plants. Rooted cuttings had been planted into 13 cm pots in week 15 2022. The plants were not pinched.

Figure 2:
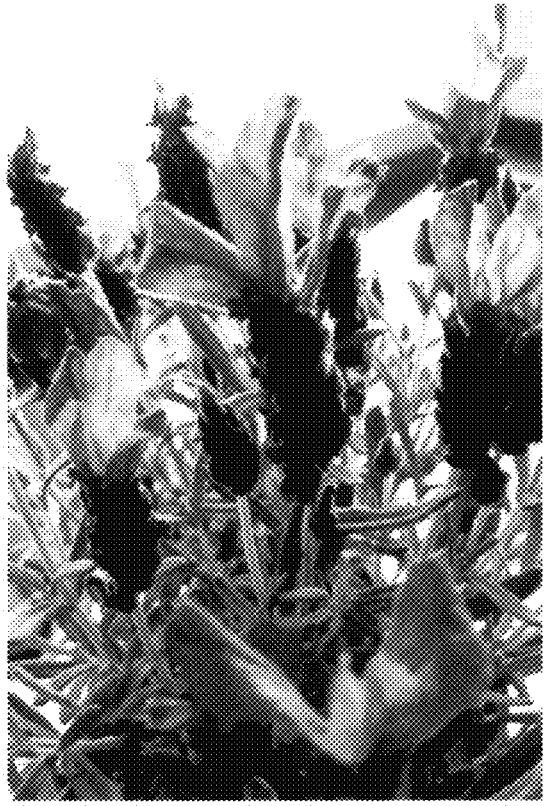

The aforementioned photographs: FIGS. 1 and 2 were taken in Enkhuizen, The Netherlands on Aug. 4, 2022 and showing a plant from an outdoor trial. The plant was about 14 weeks of age. Plants started flowering naturally in July.

Color references are made to The Royal Horticultural Society Colour Chart (R.H.S.) 2001.

TABLE 1

DIFFERENCES BETWEEN THE NEW VARIETY 'LABZ0012' AND A MOST SIMILAR VARIETY (data collected from a side-by-side grown comparison trial in 2022)

| | 'LABZ0012' | 'LABZ0004' (U.S. Plant Pat. No. 27,493) |
|---|---|---|
| Plant size: | 20 cm | Bushy, 30 cm |
| Size of bracts: | 3 cm | 5-6 cm |
| Number of bracts per inflorescence: | 4 | 7 to 12 |
| Bract color: | RHS 78A | RHS N86C |

Plant:

*Plant spread.*—15-20 cm.

*Plant height.*—20 cm, to top of flowering plane. 18 cm to top of foliar plane.

*Growth rate.*—Fast.

*Plant vigor.*—Moderate.

*Length of primary lateral branches.*—15 cm.

*Diameter of lateral branches.*—0.3 cm.

*Quantity of lateral branches.*—25.

*Plant habit.*—Dense upright shape.

Stem:

*Juvenile color.*—RHS 137C.

*Mature color.*—RHS 137A.

*Texture/pubescence.*—Smooth/No pubescence.

*Shape.*—Round.

*Strength.*—Very strong and flexible.

*Internode length.*—1.3-1.9 cm.

Propagation and roots:

*Time to initiate roots.*—About 10 days at 21 degrees C., relatively slow.

*Time to produce a rooted cutting.*—About 18-23 days at 21 degrees C.

*Root description.*—Fine, fibrous, developing a woody texture with age, slow rooter.

*Color.*—RHS 175B/155D.

Foliage:

*Leaf.*—

*Arrangement.*—Opposite.

*Leaf type.*—Simple.

*Quantity.*—Approximately 40 fully expanded per main branch and approximately 50 juvenile leaves.

*Length.*—3 cm.

*Width.*—0.5 cm.

*Shape of blade.*—Oblong.

*Apex.*—Acute.

*Base.*—Truncate.

*Attachment.*—Sessile.

*Margin.*—Entire.

*Texture of all surfaces.*—Smooth.

*Leaf fragrance.*—Very strong lavender scent.

*Color.*—

*Young foliage upper side.*—RHS 137B.

*Young foliage under side.*—RHS 137C.

*Mature foliage upper side.*—RHS 137A.

*Mature foliage under side.*—RHS 137B.

*Venation.*—Reticulate.

*Venation color upper side.*—RHS 144A, only main vein distinguishable from foliage color.

*Venation color under side.*—RHS 137B.

*Petiole.*—Absent.

Inflorsecence:

*Blooming period.*—Early summer to late summer.

*Form and shape.*—Small single flower in verticillasters arranged in spikes. Most commonly 8-10 rows of flowers. Flowers have small bracts, and medium terminal bracts. One flower spike per lateral stem.

*Number of individual flowers per spike.*—Approximately 100-125.

*Fragrance.*—None.

*Flower lastingness.*—Individual flowers last approximately 1 week, inflorescence remain ornamental for 6 weeks.

*Inflorescence size, excluding terminal bracts.*—

*Length.*—4.0 cm.

*Width.*—1.2 cm.

*Shape.*—Cylindrical.

Bud:

*Length.*—0.5 cm.

*Diameter.*—0.2 cm.

*Shape.*—Ovate.

*Color.*—RHS 77A.

*Rate of opening.*—Varies with climactic conditions: 3-7 days from colored bud to open flower.

Corolla:

*Corolla shape.*—Salverform.

*Petal number.*—5.

*Petals fused or unfused.*—Fused at base.

*Petal apex.*—Obtuse.

*Petal base.*—Fused.

*Petal shape.*—All 5 lobes ovate.

*Petal margin.*—Entire.

*Petal surfaces.*—Glabrous.

*Length.*—0.7 cm (corolla tube).

*Diameter.*—0.2 cm (corolla tube).

*Coloration of individual flowers, excluding terminal bracts.*—Immature: RHS 155B (bottom half) RHS N86A (top half). Mature: RHS 155B (bottom half) RHS N86A (top half).

Bracts:

*Bract shape.*—Elliptic.

*Bract apex.*—Acute.

*Bract color.*—RHS 137B.

*Terminal bracts (sterile).*—

*Quantity.*—4 large and 1 or 2 smaller per inflorescence.

Large (terminal) bracts:

*Length.*—3.0 cm.

*Width.*—1.0 cm.

*Form.*—Petaloid.

*Margin.*—Entire and undulating.

*Surface.*—Smooth.

*Appearance.*—Matte.

*Shape.*—Oblanceolate.

*Apex.*—Retuse.

*Base.*—Attenuate.

*Vein pattern.*—Reticulate.

*Color.*—

*Upper side of immature bract.*—RHS N78A Veins lighter.

*Under side of immature bract.*—RHS N78B Veins lighter.

*Upper side of mature bract.*—RHS N78A.

*Under side of mature bract.*—RHS N78A.

Small bracts:

*Quantity.*—1 or 2.

Calyx:

*Width.*—0.2 cm.

*Length.*—0.5 cm.

*Shape.*—Flattened tube.

*Color.*—RHS 145A/187B.

Peduncle:

*Peduncle length.*—12-15 cm.

*Peduncle diameter.*—0.3 cm.

*Aspect.*—Upright.

*Color.*—RHS 137B.

*Texture.*—Densely pubescent.

Reproductive organs:

*Androecium.*—Stamens: 4. Anther length: 0.05 cm. Anther color: RHS N155A. Pollen quantity: Pollen production not observed.

*Pistil.*—Number: 1. Length: 0.4 cm.

*Style.*—Length: 0.3 cm. Color: RHS N155A.

*Stigma.*—Length: 0.05 cm. Color: RHS N77C.

*Ovary.*—Minute and immeasurable.

Other characteristics:

*Seeds and fruits.*—Few seeds, 0.05 cm, dark brown.

*Disease/pest resistance.*—Neither resistance nor susceptibility to the normal diseases and pests of *Lavandula stoechas* has been observed.

*Drought tolerance and cold tolerance.*—Hardy perennial. Tolerates high temperature to at least 36 degrees C. While specific drought tolerance has not been observed, once plants are established very little water is necessary to maintain plants.

What is claimed is:

1. A new and distinct cultivar of *Lavandula* plant named 'LABZ0012', as substantially illustrated and described herein.

* * * * *